United States Patent
Chen et al.

(10) Patent No.: US 6,454,789 B1
(45) Date of Patent: Sep. 24, 2002

(54) PATIENT PORTABLE DEVICE FOR PHOTODYNAMIC THERAPY

(75) Inventors: James Chen, Bellevue, WA (US); Brian Wilkerson, Issaquah, WA (US); Dave Brown, Enum Claw, WA (US); Darrin Huston, Enum Claw, WA (US); Mike McQuade, Issaquah, WA (US)

(73) Assignee: Light Science Corporation, Issaquah, WA (US)

(*) Notice: Subject to any disclaimer, the term of this patent is extended or adjusted under 35 U.S.C. 154(b) by 0 days.

(21) Appl. No.: 09/232,129

(22) Filed: Jan. 15, 1999

(51) Int. Cl.[7] .................................................. A61N 5/06
(52) U.S. Cl. ........................ 607/88; 362/572; 362/574; 607/93
(58) Field of Search .................... 607/88–93; 606/2, 606/2.5, 7, 9, 10, 13–16; 604/19–21; 362/551, 554, 558, 572, 524, 32

(56) References Cited

U.S. PATENT DOCUMENTS

| | | | |
|---|---|---|---|
| 4,693,556 A | | 9/1987 | McCaughan, Jr. |
| 4,823,244 A | * | 4/1989 | Alaybayoglu et al. ...... 362/194 |
| 4,998,930 A | | 3/1991 | Lundahl |
| 5,026,367 A | * | 6/1991 | Leckrone et al. .............. 606/7 |
| 5,263,925 A | * | 11/1993 | Gilmore, Jr. et al. |
| 5,344,434 A | | 9/1994 | Talmore |
| 5,445,608 A | * | 8/1995 | Chen et al. .................... 604/20 |
| 5,456,661 A | * | 10/1995 | Narciso, Jr. .................. 604/20 |
| 5,474,528 A | | 12/1995 | Meserol |
| 5,514,669 A | * | 5/1996 | Selman ......................... 514/63 |
| 5,519,534 A | | 5/1996 | Smith et al. |
| 5,571,152 A | | 11/1996 | Chen et al. |
| 5,616,140 A | * | 4/1997 | Prescott |
| 5,634,711 A | | 6/1997 | Kennedy et al. |
| 5,645,562 A | | 7/1997 | Hann et al. |
| 6,138,681 A | | 10/1997 | Chen et al. |
| 5,700,243 A | | 12/1997 | Nariso, Jr. |
| 5,702,432 A | | 12/1997 | Chen et al. |
| 5,707,401 A | * | 1/1998 | Talmore ....................... 607/88 |
| 5,709,653 A | | 1/1998 | Leone |
| 5,715,837 A | | 2/1998 | Chen |
| 5,735,817 A | * | 4/1998 | Shantha |
| 5,741,316 A | | 4/1998 | Chen et al. |
| 5,746,494 A | * | 5/1998 | Koeda et al. ................ 362/255 |
| 5,746,495 A | * | 5/1998 | Klamm ........................ 362/183 |
| 5,766,222 A | | 6/1998 | Petit |
| 5,766,234 A | | 6/1998 | Chen et al. |

(List continued on next page.)

FOREIGN PATENT DOCUMENTS

| | | |
|---|---|---|
| AU | 0720815 | 6/1987 |
| AU | 0674251 | 6/1994 |
| AU | 0694868 | 3/1996 |

(List continued on next page.)

OTHER PUBLICATIONS

Dr. William P. Latham, et al., "Biophotonics Applications of High–Power Semiconductor Diode Laser technology", 1998.*

(List continued on next page.)

*Primary Examiner*—Roy D. Gibson
(74) *Attorney, Agent, or Firm*—Heller Ehrman White & McAuliffe LLP; Stephanie Seidman (57) ABSTRACT

A patient portable photodynamic therapy device securable to a patient includes a lightweight rechargeable battery and a cold cathode fluorescent (CCF) tube powered thereby. The CCF tube is coupled in light channeling relation to a proximal portion of a biocompatible optical fiber, which includes a distal portion with an optional diffuser that uniformly distributes light as it exits the distal portion. The distal end of the optical fiber is optionally provided with an anchoring balloon that can be inflated after the optical fiber is properly positioned at a treatment site within a patient's body. The balloon securely lodges the distal portion within the tissue at the treatment site, and is deflated to facilitate the removal of the optical fiber once the treatment is complete.

54 Claims, 7 Drawing Sheets

U.S. PATENT DOCUMENTS

| | | | |
|---|---|---|---|
| 5,769,844 A | | 6/1998 | Ghaffari |
| 5,776,175 A | * | 7/1998 | Eckhouse et al. |
| 5,782,896 A | | 7/1998 | Chen et al. |
| 5,797,868 A | * | 8/1998 | Leone |
| 5,800,478 A | | 9/1998 | Chen et al. |
| 5,803,575 A | * | 9/1998 | Anems et al. ............ 362/32 |
| 5,814,008 A | | 9/1998 | Chen et al. |
| 5,827,188 A | | 10/1998 | Chen et al. |
| 5,835,648 A | * | 11/1998 | Narciso, Jr. et al. .......... 385/31 |
| 5,843,143 A | * | 12/1998 | Whitehurst |
| 5,865,840 A | | 2/1999 | Chen |
| 5,876,427 A | | 3/1999 | Chen et al. |
| 5,906,579 A | * | 5/1999 | Vander Salm et al. ...... 600/424 |
| 5,913,834 A | * | 6/1999 | Francais ................. 600/591 |
| 5,919,217 A | * | 7/1999 | Hughes ................. 607/90 |
| 5,921,244 A | | 7/1999 | Chen et al. |
| 5,945,762 A | | 8/1999 | Chen et al. |
| 5,957,960 A | | 9/1999 | Chen et al. |
| 5,961,543 A | * | 10/1999 | Waldmann ............... 607/88 |
| 5,976,175 A | * | 11/1999 | Hirano et al. |
| 5,989,245 A | * | 11/1999 | Prescott ............... 606/14 |
| 5,997,569 A | | 12/1999 | Chen et al. |
| 5,997,842 A | | 12/1999 | Chen |
| 6,021,347 A | * | 2/2000 | Herbst et al. |
| 6,080,160 A | | 6/2000 | Chen et al. |
| 6,092,531 A | | 7/2000 | Chen et al. |
| 6,096,066 A | * | 8/2000 | Chen et al. ............... 607/88 |
| 6,135,620 A | * | 10/2000 | Marsh ................. 362/377 |
| 6,210,425 B1 | | 4/2001 | Chen |
| 6,238,426 B1 | | 5/2001 | Chen |
| 6,273,904 B1 | | 8/2001 | Chen et al. |
| ,046,983 A1 | | 11/2001 | Pandey et al. |
| 6,319,273 B1 | | 11/2001 | Chen et al. |
| 6,331,744 B1 | | 12/2001 | Chen et al. |
| ,010,500 A1 | | 1/2002 | Chen |
| 6,334,050 B1 | | 2/2002 | Skärby |
| 2001/0049502 A1 | | 12/2001 | Chen |

FOREIGN PATENT DOCUMENTS

| | | |
|---|---|---|
| AU | 0708410 | 2/1997 |
| AU | 0713227 | 9/1997 |
| AU | 0721857 | 4/1999 |
| JP | 51-159879 | 7/1978 |
| JP | 57-185220 | 11/1982 |
| WO | 9732520 | 9/1997 |
| WO | 9806456 | 2/1998 |
| WO | 9808565 | 3/1998 |
| WO | 9814243 | 4/1998 |
| WO | 9824371 | 6/1998 |
| WO | 9824510 | 6/1998 |
| WO | 9832491 | 7/1998 |
| WO | 9832492 | 7/1998 |
| WO | 9832493 | 7/1998 |
| WO | 9846130 | 10/1998 |
| WO | 9850034 | 11/1998 |
| WO | 9856302 | 12/1998 |
| WO | 9918879 | 4/1999 |
| WO | 9920346 | 4/1999 |
| WO | 9939769 | 8/1999 |
| WO | 9958149 | 11/1999 |
| WO | 9852565 | 12/1999 |
| WO | 9966988 | 12/1999 |
| WO | 0015296 | 3/2000 |
| WO | 0036983 | 6/2000 |
| WO | 0041725 | 7/2000 |
| WO | 0041726 | 7/2000 |
| WO | 0041727 | 7/2000 |
| WO | 0041768 | 7/2000 |
| WO | 0103770 | 1/2001 |
| WO | 0105316 | 1/2001 |
| WO | 0115694 | 3/2001 |
| WO | 0151087 | 7/2001 |

OTHER PUBLICATIONS

Fact Sheet: Laser Medical Pac, Jan. 1998.*

Nakatani, Y. et al., (1981) "Chemistry and biochemistry of Chinese drugs. VII. Cytostatic pheophytins from silkworm excreta, and derived photocytotoxic pheophorbides" *Chem. Pharm. Bull.* 29(8):2261–2269.

Yamamoto, T. (Dec. 10, 1974) "Effect of phytochlorin on transplantable cancer cells" *Medicine and Biology* 89(6):433–438, English translation and certificate of translation included, 7 pages.

Yamamoto, T. (Apr. 10, 1974) "Suppression of tumors by the photodynamic action of phytochlorin sodium" *Medicine and Biology* 90(4):161–164, English translation and certificate of translation included, 4 pages.

Yamamoto, T. and Miyagawa, F. (Jun. 10, 1975) "Photodynamic effects on the nucleic acids of cancer cells sensitized by sodium phytochlorin" *Medicine and Biology* 90(6):397–400, English translation and certificate of translation included, 4 pages.

Yamamoto, T. and Miyagawa, F. (1978) "Photoradiation therapy, phytochlorin and visible light" *Prevention and Detection of Cancer, Part 1, Prevention. vol. 2, Etiology–Prevention Methods* Proceedings of the Third International Symposium on Detection and Prevention of Cancer held Apr. 26, 1976 in New York, NY, 1(2):1789–1802.

Article: "Photonics Application of High–Power Semiconductor Diode Laser Technology", *AFRL Technology Horizons*, 1(1):35–36 (2000).

Bärwolff et al., "Semiconductor Diode Lasers: Research and Applications at the Max–Born–Institute", pp. 1–10 (1995).

Buda, Manuela, "Low–Confinement High–Power Semiconductor Lasers", Eindhoven University of Technology, The Netherlands (ed.), pp. 58–77 (1999).

Fukuda, Mitsuo, *Relability and Degradation of Semiconductor Lasers and LEDs*, Artech House, Inc., pp. 43–65, 115–118, and 134–136 (1991).

* cited by examiner

PATIENT PORTABLE DEVICE FOR PHOTODYNAMIC THERAPY

FIELD OF THE INVENTION

This invention relates generally to a light therapy device for activation of medicaments at one or more treatment sites within a living body, and more specifically, to photodynamic therapy devices adapted to reduce dislodgment risk over long treatment periods and enable a patient to be ambulatory without interruption of the therapy.

BACKGROUND OF THE INVENTION

Photodynamic therapy (PDT) is a two-step treatment process which has been found to be effective in destroying a wide variety of cancers. PDT is performed by first systemically or topically administering a photosensitizer compound, and subsequently illuminating a treatment site with light in a waveband, which corresponds to an absorption waveband of the photosensitizer. The light energy activates the photosensitizer compound, causing it to destroy the diseased tissue.

Numerous systems have been proposed to effectively deliver the activating light to the treatment site. Examples of such systems can be found in U.S. Pat. No. 5,519,534 issued May 21, 1996 to Smith, et al., U.S. Pat. No. 5,344,434 issued Sep. 6, 1994 to Talmore, and U.S. Pat. No. 4,693,556 issued Sep. 15, 1987 to McCaughan. The systems disclosed in these patents generally comprise a laser light source coupled to a proximal end of a flexible biocompatible optical fiber having a distal end adapted to be positioned within the body of a patient, either inside or adjacent to an internal treatment site. The optical fiber conducts and guides activating light from the laser light source to the treatment site at the distal end of the optical fiber. A diffuser enclosing the distal end of the optical fiber diffuses the light, and thus delivers the light to the treatment site at a uniform intensity to effect activation of the photosensitizer compound. In these systems, the diffuser may comprise a sphere positioned on the distal end of the fiber and having an inner partially reflective surface that aids in diffusing light transmitted through the sphere. Other light delivery devices can be found, for example, in U.S. Pat. No. 5,709,653 issued Jan. 20, 1998 to Leone, U.S. Pat. No. 5,700,243 issued Dec. 23, 1997 to Nariso, and U.S. Pat. No. 5,645,562 issued Jul. 8, 1997 to Hann, et al., and U.S. Pat. No. 4,998,930 issued Mar. 21, 1991 to Lundahl. While disclosing systems that are generally similar to the aforementioned systems, these references described diffusers that have an added component. The diffusers of these devices either alternatively or additionally incorporated transparent balloons mounted coaxially around the distal end of the optical fiber. Once the distal end is positioned at the treatment site, the balloon may be inflated in order to increase the area of the treatment site which will be exposed to the activating light, and in some cases, to effect or at least aid in the diffusion of the activating light. Once the light therapy provided by delivery of the light to the treatment site is completed, the balloon may be deflated, and the optical fiber removed from the body of the patient.

A conventional PDT treatment is of very short duration, on the order of minutes, and is typically used to treat superficial and small volume lesions. In order to apply PDT successfully against large lesions, which may be located subcutaneously, more extended treatment sessions must be undertaken. Extending the time of treatment overcomes tumor resistance and enables the extent of the treatment site to be greatly enlarged, thus allowing effective therapy of a much greater tumor volume. Indeed, destruction of a large tumor volume by extended duration PDT has been demonstrated in a clinical treatment. The treated patient suffered from a very large retroperitoneal tumor, which had eroded through the skin. The protruding tumor was treated by inserting multiple light emitting probes, such as is described in commonly assigned U.S. Pat. No. 5,445,608, into the substance of the tumor. The probes were energized for more than forty hours after orally administering a dose of a photosensitizer called aminolevulinic acid. This treatment resulted in destruction of just under one-half kilogram of tumor mass over the ensuing four weeks.

While adequate for some applications, the lasers, other high-powered light sources, and optical fibers in current use for administering PDT to a treatment site suffer several drawbacks related to safety and their inability to accommodate the extended sessions necessary to effectively treat large tumors. First, high-powered sources such as dye lasers, laser diodes, large light emitting diode (LED) arrays, incandescent sources, and other electroluminescent devices are not efficient in converting electrical energy into light energy. They generate significant amounts of heat, and consume a substantial amount of electrical power. Prolonged use of high intensity light sources can lead to inadvertant tissue damage due to the effect of the high intensity light. Further, certain of these devices, e.g. laser light sources, generate sufficient heat that they must be cooled while activated. The need for cooling necessitates the incorporation of additional hardware such as fans cooling units that draw additional power from the main power supply.

Second, the amount of power consumed by high intensity light sources requires that they be supplied with power from an alternating current (AC) line power source. Movement by the patient or attendance efforts by hospital personnel during the treatment period that cause the patient to move can inadvertently disconnect or damage the power cord, not only interrupting the treatment, but also creating a risk of electric shock. Further, being tethered to a substantially fixed power source limits the application of optical extended treatments, inasmuch as the patient will invariably need to move or be moved during the treatment period. Movement of the patient will likely cause the treatment to be interrupted and thus, render it less effective.

Third, none of the prior art techniques for rendering PDT to an internal treatment site through an optical fiber provides an anchoring mechanism to effectively secure the optical fiber and its distal end within the body of the patient at the treatment site. Any movements by the patient or attendance efforts by hospital personnel during the treatment period could inadvertently pull or dislodge the optical fiber unless it is secured in place. In many cases, while it is easy to disconnect a power cable from a light source to allow the patient to temporarily move about before resuming treatment, it is not practical to remove the optical fiber from the patient's body at that time, as well. Instead, the optical fiber must remain in place while the patient moves about. Without an effective mechanism for securing the optical fiber in the patient's body and at the treatment site while the patient moves, the risk of tissue damage is increased by such activity. Not only can the tissue be torn or severe bleeding occur when the patient moves, but if the dislodgement is not so severe, that it is noticed, the distal end of the optical fiber can be displaced away from the treatment site, so that light is delivered to the wrong area in the patient's body, resulting in possibly severe and unwanted destruction of normal tissue.

Fourth, the methodology of short duration high intensity illumination has drawbacks when applied to treat moderate to large size tumors. These drawbacks include depletion of oxygen necessary for the photodynamic destruction of the tissue that has absorbed the photosynthesizer, incomplete activation of the circulating photosensitizer, mis-timing of the illumination session so that the light therapy is not administered during the peak concentration of the photosensitizer drug in the tumor, and the possible recovery of sub-lethally injured tumor cells, which were not completely destroyed due to the short treatment time.

Currently, PDT procedures using laser light sources may be performed during an operation in which a treatment site is surgically exposed, and as such, the period available for administering light therapy is approximately one to two hours at most. The extent of tumor necrosis resulting from such an illumination period is on the order of 1 to 2 centimeters in a zone radially surrounding the optical fiber. Thus, several devices have been developed in an attempt to increase the duration of PDT treatments, to enable the light therapy to continue after an incision in a patient undergoing surgery has been closed. For example, a number of solid state laser devices have been developed for administering PDT that are semi-portable. However, these devices are large, heavy, and must be transported on wheeled carts or other movable furniture. Such "desktop" or semi-portable devices suffer from the drawbacks enumerated above if employed for prolonged PDT treatment periods lasting hours. Furthermore, such light sources must remain connected to the wall power plug by power cables, and the optical fibers through which light produced by the laser is directed to an internal treatment site are prone to dislodgment.

Another light source device, disclosed in U.S. Pat. No. 5,616,140 issued Apr. 1, 1997 to Prescott, can be powered by rechargeable batteries and thus, can be worn by the patient. However, because this device generates only low power laser light, and is not designed to be coupled to optical fibers for directing the light it produces to an internal treatment site, its use is limited to superficial light therapy, e.g., to treating skin lesions. High power lasers currently used for PDT require cooling hardware, and a corresponding power source. Due to weight and size considerations, it is clearly not practical for a patient to move about pushing a high power laser, a cooling unit, and battery power supplies for the equipment sufficient to provide for a prolonged treatment session.

Accordingly, there is a need for a PDT system to administer light therapy, which reduces the risk of optical fiber dislodgement and allows a patient to move about without interruption of the PDT therapy over treatment periods lasting hours.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

SUMMARY OF THE INVENTION

The present invention is directed to a PDT device enabling efficacious treatment of relatively large tumors that are currently not treatable using conventional PDT delivery systems and methodologies and is specially adapted to reduce the risk of dislodging an optical fiber from a treatment site and when the patient moves about. The patient can thus be ambulatory without interruption of the light therapy over long treatment periods. In a preferred embodiment, the present invention comprises a belt or harness that supports and secures a lightweight rechargeable battery and a cold cathode fluorescent (CCF) tube powered thereby to a patient. The CCF tube is coupled to a proximal portion of the optical fiber. A distal portion of the optical fiber is provided with means for diffusing light as it exits the optical fiber. The distal portion of the fiber is adapted to be positioned at a treatment site within a patient's body by a medical practitioner. A balloon disposed at a distal end of the optical fiber can be inflated after the insertion of the optical fiber within the patient's body, to secure the distal portion of the fiber within the tissue at the treatment site; the balloon is deflated prior to the removal of the optical fiber, once administration of the light therapy is completed.

The present invention overcomes the limitations of the prior art PDT delivery devices in several respects. First, the use of a CCF tube provides increased effectiveness and efficiency compared to laser light sources. Light energy losses due to coupling of the light source to the optical fiber are minimized by employing a parabolic reflector and lens to focus the light into the proximal portion of the optical fiber. It is possible to obtain a greater zone of necrosis using non-laser light delivered to the tumor mass over a longer period of time, for example, 40 hours. Therefore, a CCF tube is preferred over other light sources, such as solid laser diodes, fiber lasers, LEDs, incandescent sources, halogen sources, polymeric luminescent devices or other electroluminescent devices, because CCF tube is generally more efficient in converting electrical power to light energy. As such, it not only generates a minimal amount of heat, but also consumes a minimal amount of power, thereby eliminating the need for cooling fans and large or substantially fixed power supplies. In contrast, the alternative light sources listed above suffer from lower conversion efficiencies, generate more heat, and require greater amounts of electrical power.

A second advantage is that the use of a CCF tube allows the present invention to be powered by a portable power supply that employs widely available and commonly used rechargeable batteries such as lithium ion, nickel metal hydride, and nickel cadmium rechargeable batteries, which are lightweight and inexpensive. In contrast, the need for at least some of the other types of light sources to be accompanied by cooling fans, and even cooling systems (with the need for an additional power supply to run the cooling system), makes it impractical for them to be adapted to a portable system, because they are too bulky, weigh too much, and are too expensive. It is not a trivial advantage for the present invention to be readily portable and free from being continuously linked to a stationary or permanent power source. As the present invention can be carried about by the patient on a belt or harness, there are no power cables, which can be severed or pulled from a fixed power source due to inadvertent movements by the patient. Thus, the risk of treatment interruption and electric shock is minimized. More importantly, the patient will be able to undergo optimal extended treatment sessions, as the patient will be able to move freely or be moved without interruption of the treatment. The ability of a CCF tube to be formed into various compact shapes, including "U"s, coils, spirals, and elongate forms, further facilitates the efficient administration of light to various correspondingly shaped treatment sites by the present invention and permits the system to be worn and transported by the patient easily and comfortably.

A third advantage provided by the present invention is that it enables a CCF tube to be easily coupled in light channeling relation to the proximal portion of at least one biocompatible optical fiber. The biocompatible optical fiber is flexible not only inasmuch as its distal portion can be easily positioned within the tissue of the patient at a treatment site, but also because it can accommodate movement of surrounding tissue associated with patient respiration and ambulation. A parabolic mirror positioned in partially surrounding relation to the CCF tube and a focusing lens positioned between the CCF tube and the proximal portion of the fiber cooperate to channel light into the proximal portion of the fiber. Specifically, the parabolic mirror reflects light from the CCF tube onto the focusing lens which focuses the light into the proximal portion of the optical fiber. After the light travels through the optical fiber, it is diffused at the distal portion of the optical fiber by a diffuser of the types that are well known and documented in the art. The diffusion of the light emitted from the distal portion of the optical fiber enables the light to be administered more uniformly to the treatment site to activate the photosensitive compound previously administered. The length of the optical fiber is preferably limited to that necessary to reach the treatment site, in order to minimize light loss along the length of the optical fiber. The outer coating of the optical fiber is preferably opaque to light, in order to prevent light leaking from the optical fiber activating any photosensitizer absorbed by normal tissue along the length of the fiber. Additional biocompatible optical fibers may be connected to the parabolic mirror and focusing lens coupling the light into the proximal portions of the optical fibers or alternatively, may be spliced into the biocompatible optical fiber into which the light is focused.

A fourth advantage of the present invention over the prior art devices is that it optionally includes anchoring means for securing the optical fiber and particularly, its distal portion within the body of the patient at the treatment site. The balloon mounted to the distal end of the optical fiber can be inflated with a pressurized fluid such as air that flows through a lumen that extends substantially parallel to and which is disposed within or adjacent to the optical fiber. This lumen is thus maneuverable with the optical fiber. The lumen runs substantially the length of the optical fiber, from the pressurized fluid source that is external to the patient's body to the balloon at the distal end of the optical fiber. After positioning the distal portion of the fiber within the tissue of the patient at the treatment site, the balloon is inflated to secure the distal end of the optical fiber in the tissue. The inflated balloon also tamponades any bleeding, which may occur at the distal end of the optical fiber during its insertion. Thus, any movement by the patient during the treatment will not dislodge the optical fiber or its distal portion because the balloon anchors the optical fiber in place. Similarly, movement of the distal portion of the optical fiber will thus be avoided, preventing light from being administered to healthy tissue that has absorbed the photosensitizer. Overall, the risk of damage to normal tissue is minimized, and the need for the patient to interrupt treatment before moving about is eliminated. Once treatment is complete, the balloon is deflated to facilitate removal of the optical fiber from the patient's body. It should be noted that for some applications, the distal portion of the optical fiber should preferably abut, rather than be embedded in the treatment site. This may be the case where, for example, it is undesirable or difficult to penetrate the tumor or diseased tissue. In such a situation, the balloon may be positioned at an intermediate point along the length of the optical fiber and/or in coaxially surrounding relation to the optical fiber, rather than at its distal end.

The above features and advantages of the present invention will be better understood upon a reading of the following detailed description with reference to the accompanying drawings.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

While the present invention will be described more fully hereinafter with reference to the accompanying drawings, it is to be understood that persons skilled in the art may modify the invention herein described while achieving the functions and results of the invention. Accordingly, the descriptions which follow are to be understood as illustrative and exemplary of specific structures, aspects and features within the broad scope of the present invention and not as limiting of such broad scope.

Figure 1:
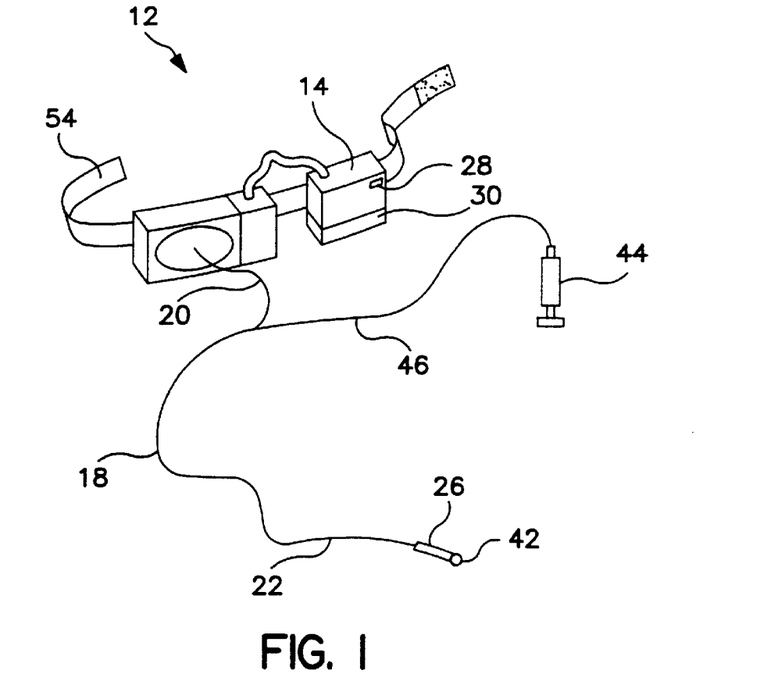
FIG. 1 is a perspective view of a patient portable PDT device according to a preferred embodiment of the present invention.
Figure 2:
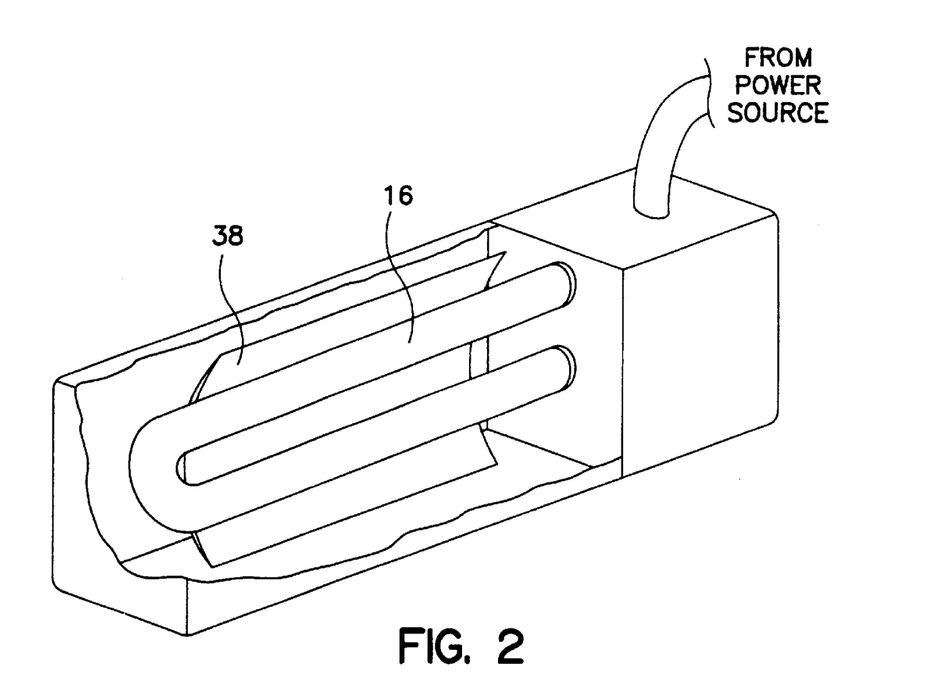
FIG. 2 is an expanded cut-away perspective view of a light source used in the patient portable PDT device, according to a preferred embodiment of the present invention.
Figure 3:
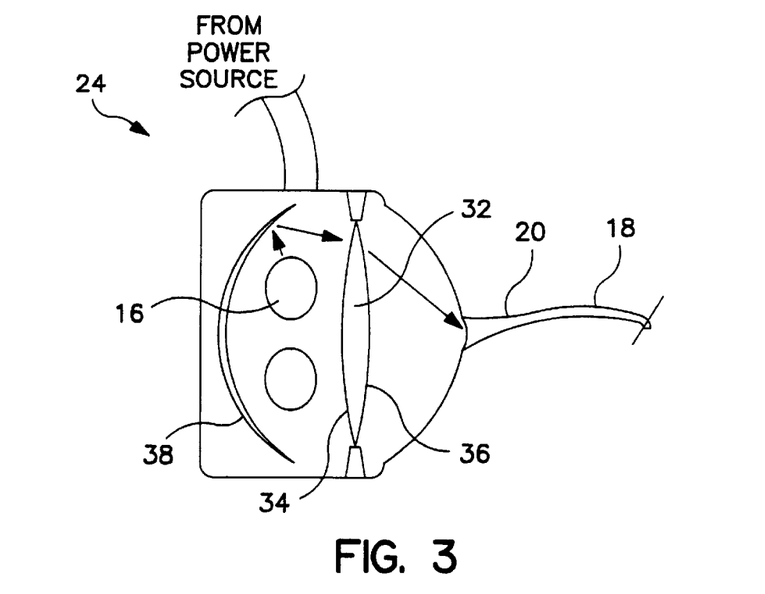
FIG. 3 is an expanded sectional view of light channeling coupling means of the patient portable PDT device, according to a preferred embodiment of the present invention.

Referring now to FIGS. 1, 2 and 3, a patient portable PDT device 12 according to the present invention comprises a power source, or lithium ion rechargeable battery pack 14; a light source, or CCF tube 16 formed into an elongated "U" shape (best shown in FIG. 2) and adapted to draw power from the battery pack 14; at least one biocompatible optical fiber 18 (only one is shown) having a proximal portion 20 and a distal portion 22, and adapted to channel light between the proximal portion 20 and the distal portion 22; and a coupling means 24 for coupling the CCF tube 16 in light channeling relation to the proximal portion 20 of the optical fiber 18 (best shown in FIG. 3). The optical fiber 18 is equipped with a diffusion means 26 (best shown in FIG. 1) for diffusing light as it exits the distal portion 22 of the optical fiber 18. The battery pack 14 includes a warning light 28 and backup power reserve 30.

It should be readily apparent to one skilled in the art, based on the instant disclosure, to alternatively use the following items in addition to or in place of their respective presently shown components, without departing from the broad scope of the present invention. For the lithium ion rechargeable battery pack 14, one may use one or more nickel cadmium rechargeable batteries, one or more nickel metal hydride rechargeable batteries, or fuel cells, any other type of electrical power source polymer batteries, one or more, other rechargeable batteries or non-chargeable batteries that are sufficiently compact and substantially lightweight to be readily portable, i.e., readily carried about by the patient. Such a power source should preferably operate at a relatively low or ambient temperature. In addition, instead of the CCF tube 16, one or more laser diodes, fiber lasers, LEDs, incandescent lights, halogen lights, polymeric luminescent devices, other types of fluorescent lights, discharge lamps, or other electroluminescent devices can be employed for the light source, including those having at least one of the characteristics of being substantially compact, substantially lightweight, operating at a substantially low temperature, or being self-contained so that the light source is suitable for a portable system that is readily carried about by the patient. For the diffusion means 26, any of the diffusers well known and documented in the prior art are suitable.

Referring now specifically to FIGS. 2 and 3, the preferred coupling means 24 employed to channel light emitted by the light source in the proximal end of the optical fiber comprises a focusing lens 32 having a convex receiver side 34 and a convex delivery side 36; and a parabolic mirror 38 positioned so that the CCF tube 16 is generally disposed at or adjacent to the focal point of the parabolic mirror. The focusing lens 32 is positioned between the CCF tube 16 and the proximal portion 20 of the optical fiber 18, so that the focusing lens receives the directly transmitted light from the CCF tube and the light reflected by the parabolic mirror 38 and focuses the light into the proximal end of the optical fiber 18. It should be readily apparent to one skilled in the art, based on the instant disclosure, to alternatively use in addition to or in place of the components disclosed for coupling means 24, one or more mirrors, concave lenses, or convex lenses, in appropriate configurations that channel light emitted by the light source into the proximal portion of the optical fiber, without departing from the broad scope of the present invention.

Figure 4:
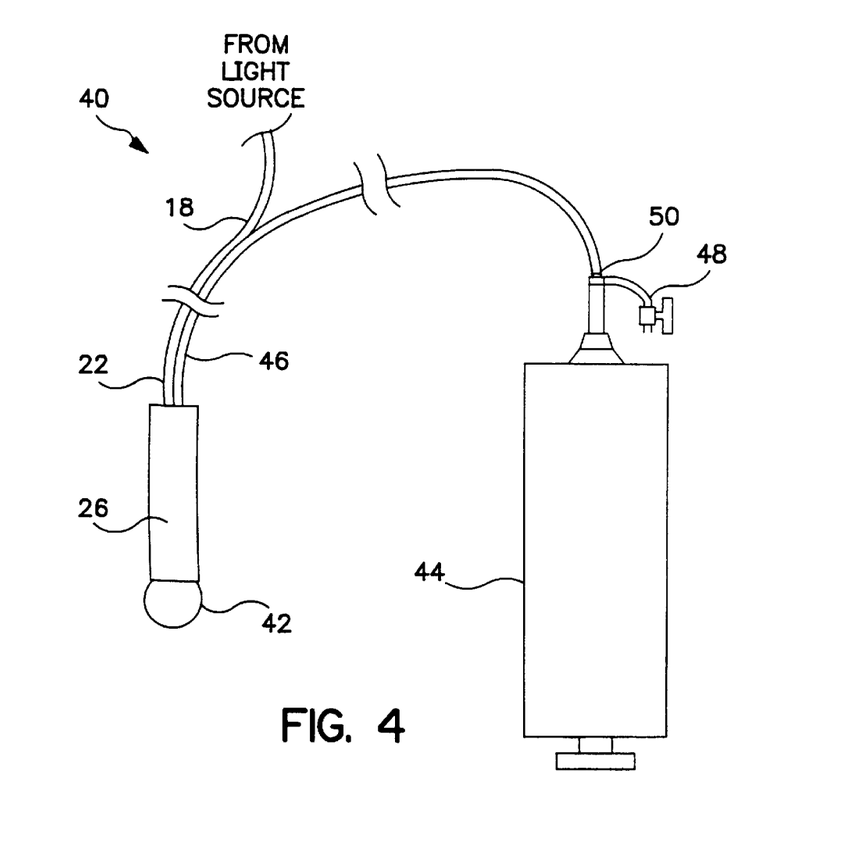
FIG. 4 is an expanded view of a distal portion anchoring means of the patient portable PDT device.

Referring now also to FIG. 4, the present invention further comprises an anchoring means 40 for anchoring the distal portion 22 of the optical fiber 18 within a patient's body. The anchoring means 40 preferably comprises a balloon 42 attached to the optical fiber 18, a pressurized air source 44 which may be a syringe which is configured to deliver pressurized air (or other pressurized fluid) to the balloon 42, a lumen 46 communicating between the air source 44 and the balloon 42, and a selection means, or control 48 and valve 50 for selectively delivering pressurized air from the pressurized air source 44 to the balloon 42 and exhausting the pressurized air from the balloon 42, so as to enable the selective inflation and deflation of the balloon. In this preferred embodiment, the optical fiber 18 has a distal end 52 on which the balloon 42 is mounted. The lumen 46 extends in substantially parallel relationship to the optical fiber 18 and runs substantially the length of the optical fiber 18, affixed to the side of the optical fiber over much of its length. Alternatively, the lumen is disposed within the optical fiber. Hollow optical fibers are well known in the optical fiber prior art.

It should be readily apparent to one skilled in the art, based on the instant disclosure, that one or more balloons (or other devices inflatable with pressurized fluids), lumens (or other channels capable of transporting gases or fluids), pressurized fluid sources, and/or other types of selection means (such as valves, switches, plugs or computer-, electrically- or mechanically-controlled components), can be employed in the present invention, in various configurations and combinations, without departing from the broad scope of the present invention. For example, a heat activated shape memory metal anchor, for example, one activated by heat developed by passing an electrical current therethrough, can be employed to hold the optical fiber in place.

Figure 5:
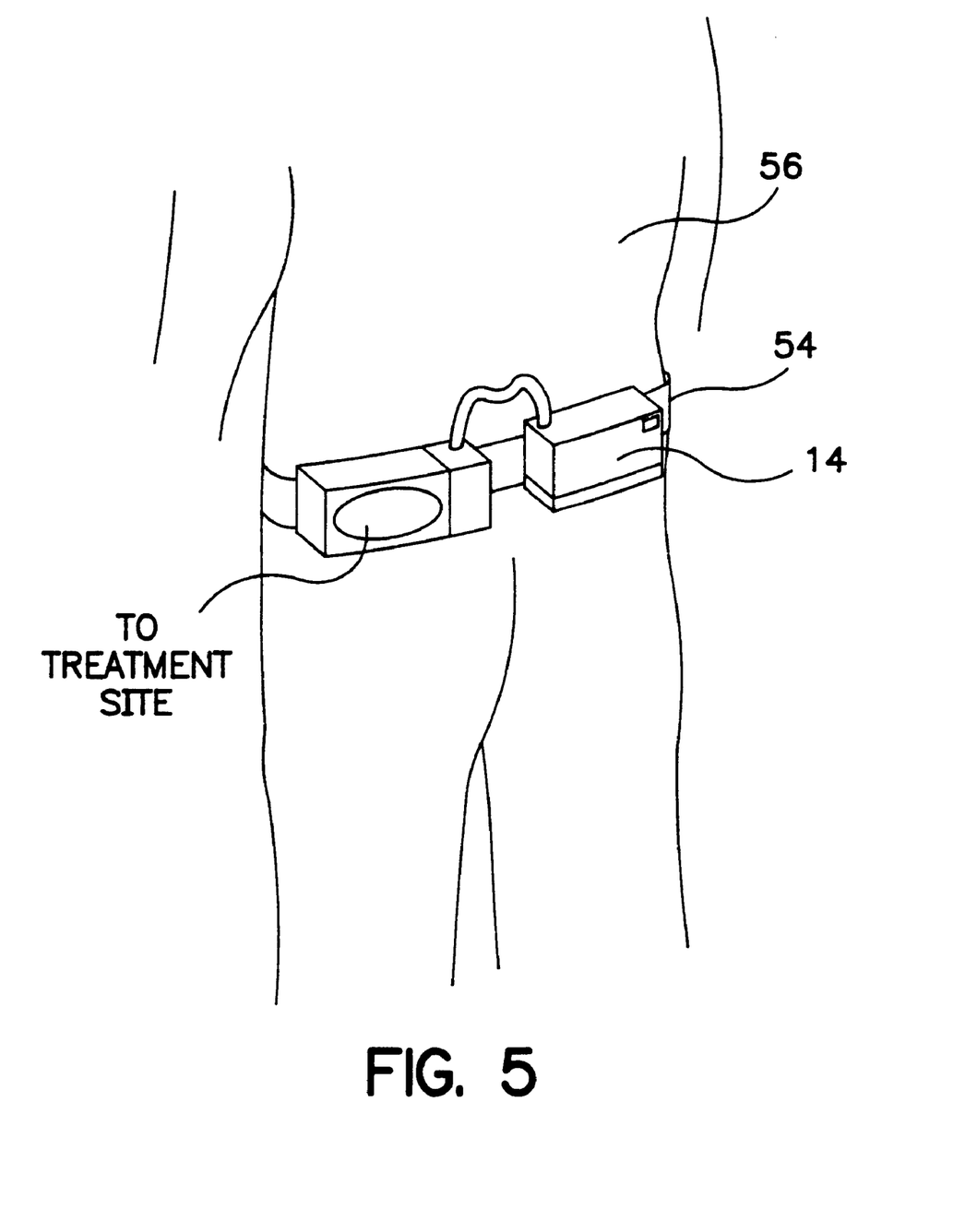
FIG. 5 is a perspective view of the patient portable PDT device being worn by a patient.

Referring now also to FIG. 5, the battery pack 14, CCF tube 16 (best shown in FIG. 2) and coupling means 24 (best shown in FIG. 3) are mounted to means for enabling a patient to easily transport the battery pack 14, CCF tube 16, and coupling means 24, i.e., at least one belt 54 (only one is shown) and are thus supported and substantially secured to a patient's body 56 as shown. While the pressurized air source 44 (best shown in FIG. 4) can also be mounted to the belt 54 an thus supported and substantially secured to a patient's body 56, it is likely that the air source, preferably a syringe will be used to initially inflate the balloon after the distal end of the optical fiber is properly positioned at the treatment site and thereafter be disconnected, provided that the pressurized fluid is retained within balloon until the optical fiber can be removed from the patient after the treatment is completed. It should be readily apparent to one skilled in the art, based on the instant disclosure, to alternatively use in addition to or in place of belt 54, one or more other belts, one or more harnesses, vests, straps, pockets, flaps, buckles, or hook-and-loop or other connection straps, in various combinations and configurations, to secure at least the light source and portable power supply to the patient's person, without departing from the broad scope of the present invention.

Figure 6:
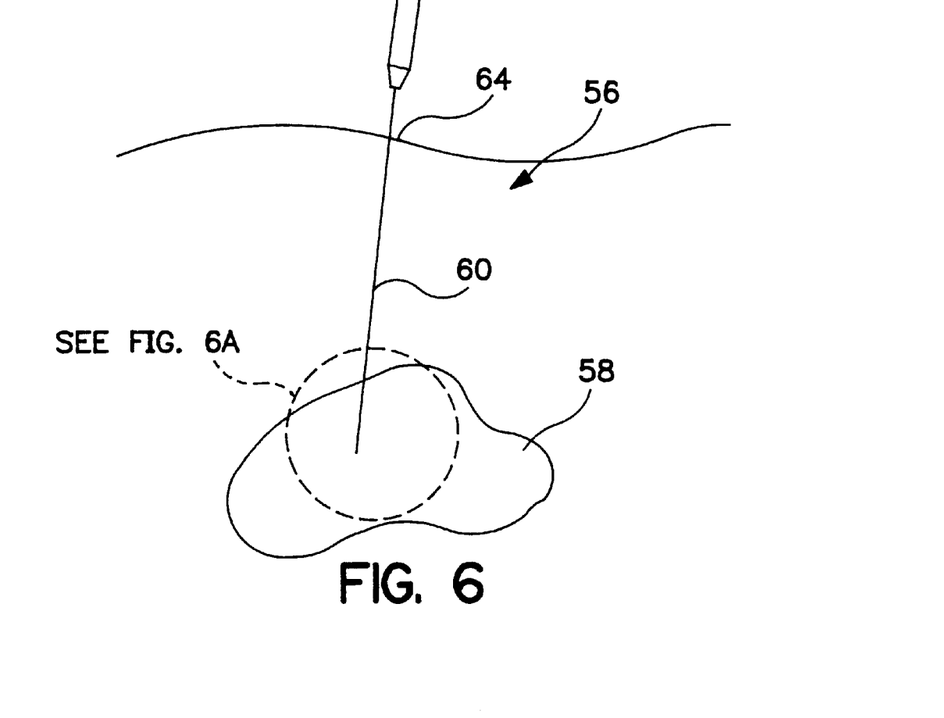
FIG. 6 is a cut away illustration of the positioning of a needle having a peel away sheath that is employed for inserting an optical fiber used in the patient portable PDT device.
Figure 6A:
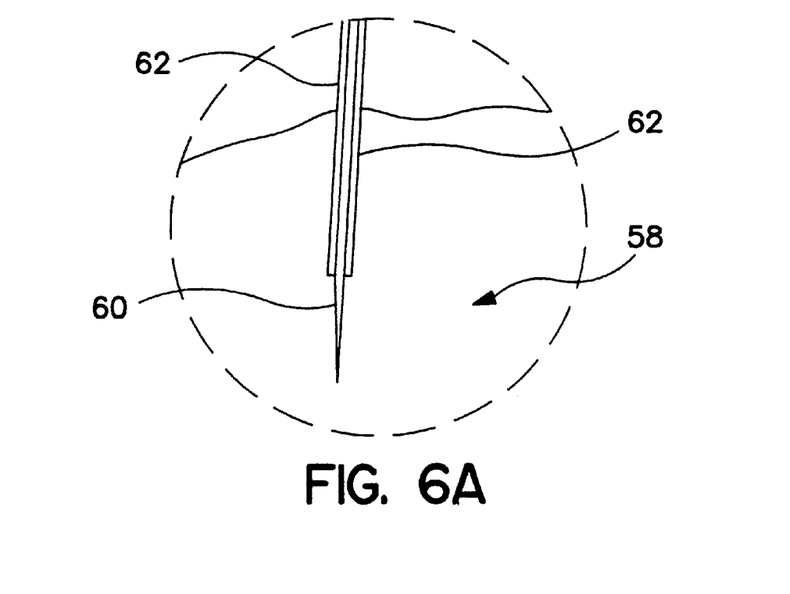
Figure 7:
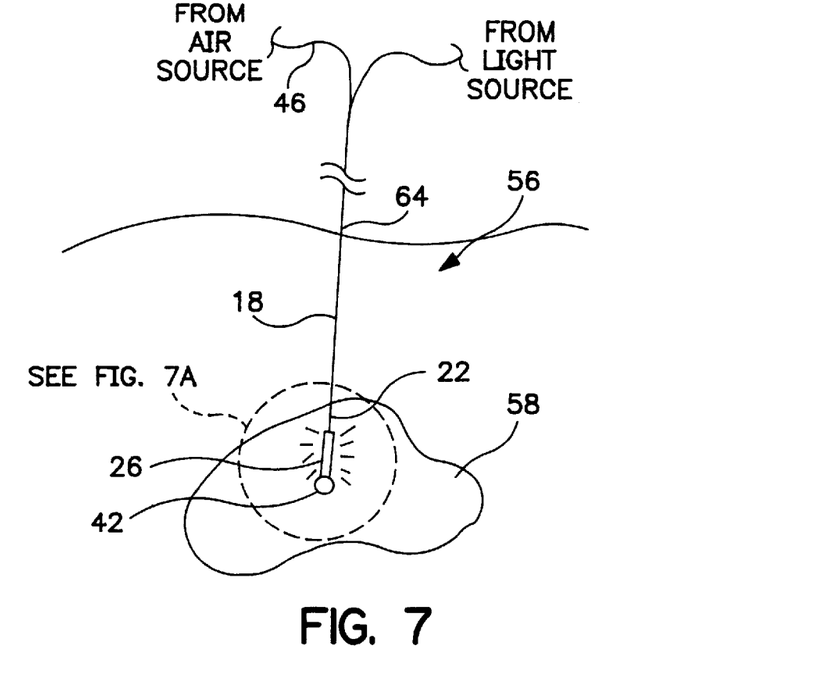
FIG. 7 is a cutaway illustration of the positioning and anchoring of a distal portion of the optical fiber.
Figure 7A:
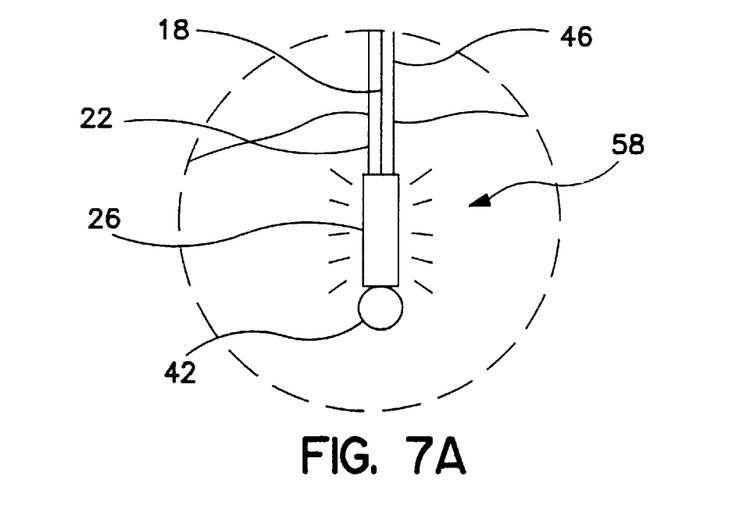

Referring now to FIGS. 6 and 7, after the photosensitizer drug (not shown) is administered to the treatment site 58 within the patient's body 56 (not shown in full), a needle 60 having a peel away sheath 62 is inserted into the patient's body while observed using an appropriate imaging system (such as CT, Ultrasound, MRI, X-ray) to the treatment site 58 within the patient's body 56 (not shown in full). Though image guidance is preferred for achieving an accurate disposition of the optical fiber, it is optional and is not necessary, especially for disposition of the optical fiber to treat superficial lesions. The needle 60 is removed and the optical fiber 18 with the balloon 42 deflated is passed through the peel away sheath which was previously properly positioned at the treatment site. The position of the distal portion 22 is confirmed via the imaging modality used to pass the needle 60, and the peel away sheath 62 is pulled up and split apart. The position of the distal portion 22 is then reconfirmed. The proximal portion of the optical fiber 18 is secured to the skin of the patient at an exit point 64 by way of suture, adhesive tape, or other fixation means (not shown). The pressurized air source 44 (best shown in FIG. 4) is coupled to the lumen 46, and pressurized air from the pressurized air source 44 is delivered to the balloon 42 in volume sufficient to inflate the balloon 42 so as to anchor the distal portion 22 of the optical fiber 18 at the treatment site 58 and tamponade any bleeding, which may have occurred during the introduction of the optical fiber 18 into the patient's body. Once the balloon 42 is sufficiently inflated, the pressurized air source 44 is uncoupled from the lumen 46. The pressurized air is prevented from escaping from the lumen 46 by the valve 50 (best seen in FIG. 4). Any dislodgment or displacement of the optical fiber 18 or its distal portion 22 due to movement of the patient will be resisted by the inflated balloon 42.

Once the balloon 42 has been inflated, the patient fastens the belt 54 (best shown in FIG. 5), which supports and secures the battery pack 14, CCF tube 16 (best shown in FIG. 2), and coupling means 24 (best shown in FIG. 3) to the patient. The battery pack 14, CCF tube 16, and coupling means 24 collectively are sufficiently compact and lightweight to be easily transported by the patient, and movement about by the patient during extended treatments is thus greatly facilitated. The CCF tube 16 is coupled to the battery pack 14 so as to draw electrical power. The proximal portion 20 of the optical fiber 18 is coupled to the CCF tube 16 by the coupling means 24 (best shown in FIG. 3). Other coupling means are possible as well, such as those described in U.S. Pat. No. 5,769,844. Different lengths of optical fiber 18 are available so that the shortest length possible can be employed to minimize light loss. A slight amount of slack in the optical fiber is allowed so that bending, twisting, turning, and other movements by the patient are accommodated. To begin treatment, the CCF tube 16 is activated with electrical current from the battery pack. As best shown in FIG. 3, a quantity of light from the CCF tube 16 is reflected by the parabolic mirror 38 onto the receiver side 34 of the focusing lens 32. The focusing lens 32 focuses light from the parabolic reflector and from the CCF tube into the proximal portion 20 of the optical fiber 18. The light is channeled through the optical fiber 18 to the distal portion 22 of the optical fiber 18, where it exits the distal portion 22 and is diffused by the diffusion means 26. This diffused light is thus delivered to the treatment site 58 in a uniform manner.

The battery pack 14 preferably provides at least 2 to 3 hours of operating time, depending on the power consumption of the light source, before it must be recharged. However, inasmuch as it is removable and modular, it can be immediately replaced with a fresh battery pack and later recharged without interruption of the therapy. Once the battery pack 14 begins to lose power, the warning light 28 on the battery pack 14 alerts the patient that the battery pack 14 must be replaced soon. The backup power reserve 30 provides the CCF tube 16 with power while the patient replaces the battery pack 14 with a fresh battery pack (not shown).

Once treatment is complete, or in the event that treatment must be halted prior the completion, the CCF tube 16 can be deactivated, the optical fiber 18 can be uncoupled from the coupling means 24, and the valve 50 can be opened to allow the pressurized air in the balloon 42 to escape, to deflate the balloon 42. Under the supervision of medically trained personnel, the suture or adhesive tape securing the proximal portion of the optical fiber 18 to the patient's body 56 at the exit point 64 can be removed, and the optical fiber 18 can be withdrawn from the patient+s body.

Figure 8:
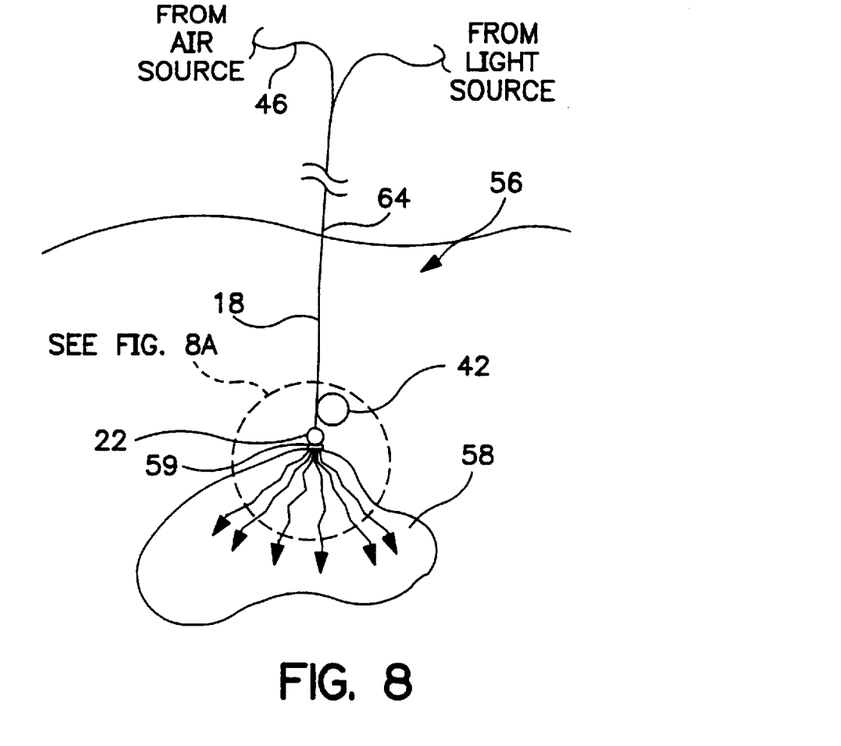
FIG. 8 is cutaway illustration of the positioning and anchoring of the distal portion of the optical fiber.
Figure 8A:
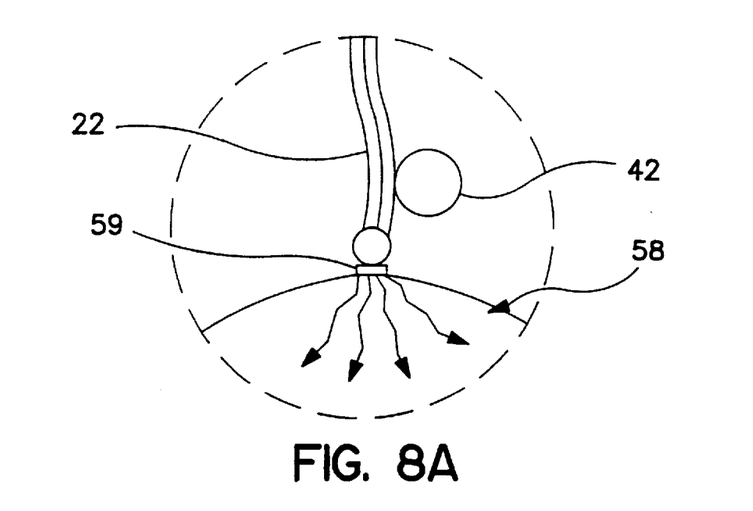

Referring now to FIG. 8, alternate preferred embodiments may incorporate a different positioning of the balloon 42, such as at an intermediate point along the length of the optical fiber 18 to enable the distal portion 22 of the optical fiber 18 to abut a treatment site 58 as shown, rather than to be inserted within the treatment site 58. In this embodiment, light is directed toward the treatment site by a microlens 59 attached to the distal end of the fiber optic. The lens 59 enables light to be focused onto the peripheral boundary of the treatment site and penetrate into its depths without actually having to insert the fiber optic into the treatment site. Administering light therapy to the surface of the treatment site is preferable when the site should not be punctured with a needle, such as in the care of a highly vascular lesion, which would bleed excessively if the needle passed through a blood vessel.

Referring again to FIGS. 1 and 7, another aspect of the present invention is directed to a method for delivering light to a treatment site, comprising the steps of employing the power source, or battery pack 14 to energize the light source, or CCF tube 16; coupling the CCF tube 16 in light channeling relation to the proximal portion 20 of the biocompatible optical fiber 18; positioning the distal portion 22 of the optical fiber at the treatment site 58 within a patient's body; and administering the light through the optical fiber 18 to the treatment site 58. More specifically, the CCF tube 16 can be coupled in light channeling relation to the proximal portion 20 by the coupling means 24 described in detail above and shown in FIG. 3. However, as noted above, it should be readily apparent to one skilled in the art, based on the instant disclosure that in addition to or in place of the presently shown coupling means 24, one or more mirrors, concave lenses, or convex lenses, in varying configurations can be used to channel the light into the optical fiber, without departing from the broad scope of the present invention. The distal portion 22 can be positioned at the treatment site 58 in the manner outlined in detail above and shown in FIG. 6 where a needle 60 having a peel away sheath 62 is passed under image guidance (such as CT, Ultrasound, X-ray) to the treatment site 58. After the needle 60 is withdrawn, the optical fiber 18 with the balloon 42 deflated is inserted through the peel away sheath. The position of the distal portion 22 is confirmed via the imaging modality used to position the needle 60, and the peel away sheath 62 is pulled up and split apart. The position of the distal portion 22 is then reconfirmed. However, it should be readily apparent to one skilled in the art, based on the instant disclosure, that alternative steps maybe used in addition to or in place of those described above, without departing from the broad scope of the present invention.

Figure 9:
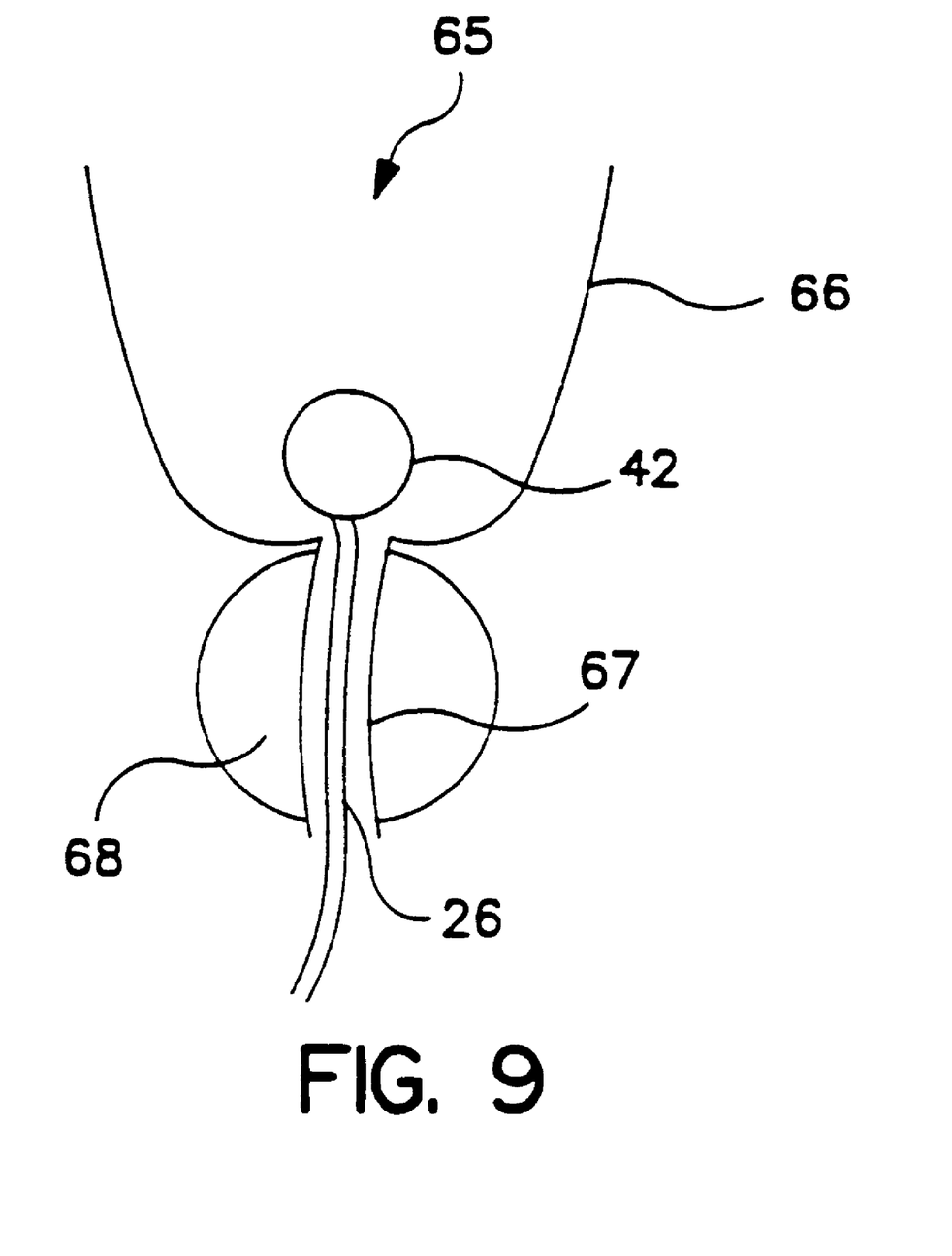
FIG. 9 is a cutaway illustration of the positioning and anchoring of the distal portion of the optical fiber in the bladder, with the light diffuser portion of the optical fiber disposed in the prostatic portion of a patient's urethra.

FIG. 9 illustrates treatment of a bladder 65 wherein the balloon 42 is inflated on the inside of the bladder wall 66 to keep the diffusion means 26 properly inserted in the urethra 67. The prostrate gland 68 is also schematically represented.

Referring now again also to FIG. 4, another aspect of the present invention is directed to a method for anchoring the distal portion 22 of the optical fiber 18 at the treatment site 58. This method includes the steps of mounting the balloon 42 to the optical fiber 18; coupling the pressurized air source 44, configured to deliver pressurized air, in selective fluid communication with the balloon 42; positioning the balloon 42 (deflated) with the distal portion 22 into the treatment site 58; and activating the pressurized air source 44 to inflate the balloon 42 after positioning of the distal portion 22 of the optical fiber at the treatment site 58. More specifically, the pressurized air source 44 can be selectively coupled in fluid communication to the balloon 42 by the lumen 46 described in detail above, and employing the control 48 and valve 50 to control the inflation and deflation of the balloon, as described.

As further explained above, the balloon 42 may be positioned at the distal end 52 of the optical fiber 18 as shown in FIG. 7, or at any intermediate point along the length of the optical fiber 18 as shown in FIG. 8. As noted above, it should be readily apparent to one skilled in the art, based on the instant disclosure, to alternatively use in addition to or in place of the components described for anchoring means 40, one or more balloons (or other devices inflatable by gases or fluids), lumens (or other channels capable of transporting gases or fluids), pressurized fluid sources (or other gas or fluid sources), and selection means (such as valves, switches, plugs, or computer-, mechanically- or electrically-controlled components, such as shape memory metal anchoring devices), in various configurations and combinations, without departing from the broad scope of the present invention.

Referring now again also to FIG. 5, yet another aspect of the present invention pertains to a method for securing the battery pack 14 and the CCF tube 16 to a patient. This method comprises the steps of securing the battery pack 14 and the CCF tube 16 to the belt 56 and attaching the belt 56 to a patient, as shown in FIG. 5. As noted above, it should be readily apparent to one skilled in the art, based on the instant disclosure, to alternatively use in addition to or in place of the belt 54, one or more other belts, harnesses, vests, straps, pockets, flaps, buckles, or hook-and-loop straps, or other connectors, in various combinations and configurations, without departing from the broad scope of the present invention.

Although the present invention has been described in connection with the preferred form of practicing it and in regard to alternative embodiments, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

What is claimed is:

1. A patient portable light therapy device, comprising:
   a portable power source that stores electrical energy;
   a light source coupled to said portable power source and adapted to be energized thereby, wherein said light source is adapted for use in a light therapy occurring over a period of time of at least two hours; and
   at least one optical fiber having a proximal portion coupled to the light source and a distal portion adapted to be disposed at a treatment site within a patient's body said at least one optical fiber conveying light emitted by the light source, wherein said light exits from the distal portion of said optical fiber and thereby administers said light therapy to the treatment site, said portable power source, said light source, and said at least one optical fiber being sufficiently light in weight and sufficiently compact so as to be readily carried about by the patient while the light source is administering the light therapy to the treatment site within the patient's body.

2. The device of claim 1, wherein at least one of said portable power source and said light source is self-contained.

3. The device of claim 1, wherein said portable power source is rechargeable.

4. The device of claim 1, wherein said portable power source comprises one of a battery and a fuel cell.

5. The device of claim 1, wherein said light source is selected from the group consisting of: one or more laser diodes, fiber lasers, LEDs, incandescent lights, halogen lights, polymeric luminescent devices, fluorescent lights, discharge lamps, and electroluminescent devices.

6. The device of claim 1, further comprising a carrier for said portable power source, and said light source.

7. The device of claim 6, wherein said carrier comprises one of a belt, a harness, and a pack adapted to support and enable a patient to carry said portable power source, and said light source.

8. The device of claim 6, wherein said carrier is adapted to be secured to a patient while the patient is moving about.

9. The device of claim 1, further comprising:
   an elastomeric membrane having a volume that is selectively varied to anchor the distal portion of said at least one optical fiber within a patients body;
   and wherein said elastomeric membrane is biocompatible.

10. The device of claim 9, wherein said elastomeric membrane comprises: a balloon attached to said at least one optical fiber; and a source of pressurized fluid that is coupled in fluid communication to selectively inflate said balloon.

11. The device of claim 10, wherein said balloon is coupled in fluid communication with the source of pressurized fluid by a fluid channel that extends along said at least one optical fiber to said balloon from the source of pressurized fluid.

12. The device of claim 11, wherein said fluid channel is substantially coaxial with said at least one optical fiber.

13. The device of claim 10, wherein said balloon is mounted around said distal portion of said at least one optical fiber.

14. The device of claim 10, wherein said balloon is mounted around said at least one optical fiber, at an intermediate point.

15. The device of claim 1, wherein said at least one optical fiber is equipped with means for diffusing light as it exits the distal portion of said at least one optical fiber.

16. A patient portable light therapy device according to claim 1, wherein the distal portion of the optical fiber is adapted to be disposed at a treatment site within a patient's body external to a lumen of the vasculature of the patient's body.

17. A patient portable light therapy device, comprising:
   a portable power source that stores electrical energy;
   a light source coupled to said portable power source and adapted to be energized thereby, wherein said light source is adapted for use in a light therapy occurring over a period of time of at least two hours;
   at least one optical fiber having a proximal portion coupled to the light source and a distal portion adapted to be disposed at a treatment site within a patient's body, said at least one optical fiber conveying light emitted by the light source, wherein said light exits from the distal portion of said optical fiber and thereby administers said light therapy to the treatment site, said portable power source, said light source, and said at least one optical fiber being sufficiently light in weight and sufficiently compact so as to be readily carried about by the patient while the light source is administering the light therapy to the treatment site within the patient's body;
   a focusing lens; and
   a parabolic mirror positioned adjacent to said light source so as to reflect a quantity of light from said light source onto the focusing lens, wherein the focusing lens is disposed between said light source and the proximal portion of said at least one optical fiber and is adapted to receive the quantity of light, transmit a portion of the quantity of light, and focus at least part of the portion of the quantity of light into the proximal portion of the optical fiber.

18. A patient portable light therapy device, comprising:
   a portable power source that stores electrical energy;
   a light source coupled to said portable power source and adapted to be energized thereby, wherein said light source comprises a non-laser light source; and
   at least one optical fiber having a proximal portion coupled to the light source and a distal portion adapted to be disposed at a treatment site within a patient's body, said at least one optical fiber conveying light emitted by the light source, wherein said light exits from the distal portion of said optical fiber and thereby administers said light therapy to the treatment site, said portable power source, said light source, and said at least one optical fiber being sufficiently light in weight and sufficiently compact so as to be readily carried about by the patient while the light source is administering the light therapy to the treatment site within the patient's body.

19. The device of claim 18, wherein said light source comprises a cold cathode fluorescent tube.

20. A patient portable light therapy device according to any of claim 1, 5, or 19, wherein the portable power source and the light source are configured to operate continuously for a period of at least two hours.

21. A patient portable light therapy device according to claim 19, wherein said device further comprises a focusing lens and a parabolic mirror positioned adjacent to said light source so as to reflect a quantity of light from said light source onto the focusing lens; and wherein the focusing lens is disposed between said light source and the proximal portion of said at least one optical fiber and is adapted to receive the quantity of light, transmit a portion of the quantity of light, and focus at least part of the portion of the quantity of light into the proximal portion of the optical fiber.

22. A patient portable light therapy device according to claim 21, wherein said device further comprises a balloon attached to said at least one optical fiber; and a source of pressurized fluid that is coupled in fluid communication to selectively inflate said balloon lumen.

23. A patient portable light therapy device according to claim 22, wherein said device further comprises a carrier selected from the group consisting of a belt, a harness, and a pack adapted to support and enable a patient to carry said portable power source said light source.

24. A patient portable light therapy device according to claim 21, wherein said at least one optical fiber is equipped with a light diffuser to diffuse the light as it exits the distal portion of at least one optical fiber.

25. A patient portable light therapy device according to claim 24, wherein said device further comprises a balloon attached to said at least one optical fiber; and a source of pressurized fluid that is coupled in fluid communication to selectively inflate said balloon lumen.

26. A patient portable light therapy device according to claim 25, wherein said device further comprises a carrier selected from the group consisting of a belt, a harness, and a pack adapted to support and enable a patient to carry said portable power source and said light source.

27. A patient portable light therapy device according to claim 18, wherein said device further comprises a focusing lens and a parabolic mirror positioned adjacent to said light source so as to reflect a quantity of light from said light source onto the focusing lens; and wherein the focusing lens is disposed between said light source and the proximal portion of said at least one optical fiber and is adapted to receive the quantity of light, transmit a portion of the quantity of light, and focus at least part of the portion of the quantity of light into the proximal portion of the optical fiber.

28. A patient portable light therapy device according to claim 27, wherein said at least one optical fiber is equipped with a light diffuser to diffuse the light as it exits the distal portion of said at least one optical fiber.

29. A patient portable light therapy device according to claim 18, wherein said at least one optical fiber is equipped with a light diffuser to diffuse the light as it exits the distal portion of said at least one optical fiber.

30. A patient portable light therapy device according to claim 29, wherein said device further comprises a balloon attached to said at least one optical fiber; and a source of pressurized fluid that is coupled in fluid communication to selectively inflate said balloon lumen.

31. The patient portable light therapy device of claim 18, wherein the portable power source and the light source are configured to operate continuously for a period of at least two hours.

32. A patient portable light therapy device, comprising:
a portable power source that stores electrical energy;
a light source coupled to said portable power source and adapted to be energized thereby, wherein said light source is adapted for use in a light therapy occurring over a period of time of at least two hours; and
at least one optical fiber having a proximal portion coupled to the light source and a distal portion adapted to be disposed at a treatment site within a patient's body, said at least one optical fiber conveying light emitted by the light source, wherein said light exits from the distal portion of said optical fiber and thereby administers said light therapy to the treatment site; and
an elastomeric membrane having a volume that is selectively varied to anchor the distal portion of said at least one optical fiber within a patient's body;
and wherein said elastomeric membrane is bio-compatible, wherein said elastomeric membrane comprises:
a balloon attached to said at least one optical fiber; and
a source of pressurized fluid that is coupled in fluid communication to selectively inflate said balloon; and
a carrier on which said portable power source, and said light source are mounted; and wherein said portable power source, and said light source being substantially compact and self-contained, said portable power source, said light source, said at least one optical fiber, and said carrier being sufficiently light in weight and sufficiently compact so as to be readily carried about by the patient while the light source is administering the light therapy to the treatment site within the patient's body.

33. The device of claim 32, wherein said carrier comprises one of a belt adapted to support and substantially secure said portable power source, and said light source to a patient.

34. The device of claim 32, wherein:
said portable power source comprises one of a battery and a fuel cell; and said light source comprises a cold-cathode fluorescent tube.

35. A patient portable light therapy device, comprising:
a portable power source that stores electrical energy;
a light source coupled to said portable power source and adapted to be energized thereby; and
at least one optical fiber having a proximal portion coupled to the light source and a distal portion adapted to be disposed at a treatment site within a patient's body external to a lumen of the vasculature of the patient's body, said at least one optical fiber conveying light emitted by the light source, wherein said light exits from the distal portion of said optical fiber and thereby administers said light therapy to the treatment site, said portable power source, said light source, and said at least one optical fiber being sufficiently light in weight and sufficiently compact so as to be readily carried about by the patient while the light source is administering the light therapy to the treatment site within the patient's body.

36. The device of claim 35, wherein at least one of said portable power source and said light source is self-contained.

37. The device of claim 35, further comprising a carrier for said portable power source, and said light source.

38. The device of claim 35, further comprising an elastomeric balloon having a volume that is selectively varied to anchor the distal portion of said at least on optical fiber within a patient's body; and wherein said elastomeric balloon is biocompatible, and a source of pressurized fluid that is coupled in fluid communication to selectively inflate said elastomeric balloon.

39. The device of claim 38, wherein said balloon is mounted around said distal portion of said at least one optical fiber.

40. The device of claim 38, wherein said balloon is mounted around said at least one optical fiber at an intermediate point.

41. The device of claim 38, wherein said balloon is coupled in fluid communication with the source of pressurized fluid by a fluid channel that extends along said at least on optical fiber to said balloon from the source of pressurized fluid and wherein said fluid channel is substantially coaxial with said at least one optical fiber.

42. A patient portable light therapy device, comprising:

a portable power source that stores electrical energy;

a light source coupled to said portable power source and adapted to be energized thereby, wherein said light source comprises a non-laser light source; and at least one optical fiber having a proximal portion coupled to the light source and a distal portion adapted to be disposed at a treatment site within a patient's body external to a lumen of the vasculature of the patient's body, said at least one optical fiber conveying light emitted by the light source, wherein said light exits from the distal portion of said optical fiber and thereby administers said light therapy to the treatment site, said portable power source, said light source, and said at least one optical fiber being sufficiently light in weight and sufficiently compact so as to be readily carried about by the patient while the light source is administering the light therapy to the treatment site within the patient's body.

43. The device of claim 42, wherein said light source comprises a cold cathode fluorescent tube.

44. A patient portable light therapy device according to any of claim 35, 42, or 43 wherein the portable power source and the light source are configured to operate continuously for a period of at least two hours.

45. A patient portable light therapy device according to claim 43, wherein said device further comprises a focusing lens and a parabolic mirror positioned adjacent to said light source so as to reflect a quantity of light from said light source onto the focusing lens; and wherein the focusing lens is disposed between said light source and the proximal portion of said at least one optical fiber and is adapted to receive the quantity of light, transmit a portion of the quantity of light, and focus at least part of the portion of the quantity of light into the proximal portion of the optical fiber.

46. A patient portable light therapy device according to claim 45, wherein said device further comprises a balloon attached to said at least one optical fiber; and a source of pressurized fluid that is coupled in fluid communication to selectively inflate said balloon.

47. A patient portable light therapy device according to claim 46, wherein said device further comprises a carrier selected from the group consisting of a belt, a harness, and a pack adapted to support and enable a patient to carry said portable power source and said light source.

48. A patient portable light therapy device according to claim 45, wherein said at least one optical fiber is equipped with a light diffuser to diffuse the light as it exits the distal portion of said at least one optical fiber.

49. A patient portable light therapy device according to claim 48, wherein said device further comprises a balloon attached to said at least one optical fiber; and a source of pressurized fluid that is coupled in fluid communication to selectively inflate said balloon.

50. A patient portable light therapy device according to claim 49, herein said device further comprises a carrier selected from the group consisting of a belt, a harness, and a pack adapted to support and enable a patient to carry said portable power source and said light source.

51. A patient portable light therapy device according to claim 42, wherein said device further comprises a focusing lens and a parabolic mirror positioned adjacent to said light source so as to reflect a quantity of light from said light source onto the focusing lens; and wherein the focusing lens is disposed between said light source and the proximal portion of said at least one optical fiber and is adapted to receive the quantity of light, transmit a portion of the quantity of light, and focus at least part of the portion of the quantity of light into the proximal portion of the optical fiber.

52. A patient portable light therapy device according to claim 51, wherein said at least one optical fiber is equipped with a light diffuser to diffuse the light as it exits the distal portion of said at least one optical fiber.

53. A patient portable light therapy device according to claim 42, wherein said at least one optical fiber is equipped with a light diffuser to diffuse the light as it exits the distal portion of said at least one optical fiber.

54. A patient portable light therapy device according to claim 53, wherein said device further comprises a balloon attached to said at least one optical fiber; and a source of pressurized fluid that is coupled in fluid communication to selectively inflate said balloon.

* * * * *

UNITED STATES PATENT AND TRADEMARK OFFICE
CERTIFICATE OF CORRECTION

PATENT NO.    : 6,454,789 B1
DATED         : September 24, 2002
INVENTOR(S)   : Chen et al.

It is certified that error appears in the above-identified patent and that said Letters Patent is hereby corrected as shown below:

Title page,
Item [73], replace "Light Science Corporation" with --Light Sciences Corporation --
Item [56], References Cited, U.S. PATENT DOCUMENTS, please replace
U.S. Patent No. "5,827,188" with -- 5,827,186 --

Column 9,
Line 49, please replace "patient+s" with -- patient's --

Column 11,
Lines 23-41, please replace claim 1 with the following claim:
1. A patient portable light therapy device, comprising:
    a portable power source that stores electrical energy;
    a light source coupled to said portable power source and adapted to be energized thereby, wherein said light source is adapted for use in a light therapy occurring over a period of time of at least two hours; and
    at least one optical fiber having a proximal portion coupled to the light source and a distal portion adapted to be disposed at a treatment site within a patient's body, said at least one optical fiber conveying light emitted by the light source, wherein said light exits from the distal portion of said optical fiber and thereby administers said light therapy to the treatment site, said portable power source, said light source, and said at least one optical fiber being sufficiently light in weight and sufficiently compact so as to be readily carried about by the patient while the light source is administering the light therapy to the treatment site within the patient's body.

Signed and Sealed this

Eighth Day of April, 2003

JAMES E. ROGAN
*Director of the United States Patent and Trademark Office*